US006410552B1

(12) United States Patent
Dodd et al.

(10) Patent No.: US 6,410,552 B1
(45) Date of Patent: Jun. 25, 2002

(54) BENZOETHER AND RELATED COMPOSITIONS AND METHODS

(75) Inventors: John H. Dodd, Pittstown, NJ (US); James R. Henry, Indianapolis, IN (US); Kenneth C. Rupert, South Orange, NJ (US); James L. Bullington, Hamilton Square, NJ (US); Daniel A. Hall, Somerset, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/751,002

(22) Filed: Dec. 28, 2000

Related U.S. Application Data

(60) Provisional application No. 60/178,388, filed on Jan. 27, 2000.

(51) Int. Cl.$^7$ ................ A61K 31/55; A61K 31/4365; C07D 497/04; A61P 9/00; A61P 11/06
(52) U.S. Cl. ............................ 514/291; 546/89
(58) Field of Search .............. 514/291; 546/89

(56) References Cited

U.S. PATENT DOCUMENTS

| | | | |
|---|---|---|---|
| 4,285,955 A | 8/1981 | Wehinger et al. | |
| 4,483,985 A | 11/1984 | Wehinger et al. | |
| 4,532,248 A | 7/1985 | Franckowiak et al. | |
| 4,845,225 A | 7/1989 | Schwender et al. | |
| 4,879,384 A | 11/1989 | Schwender et al. | |
| 5,075,440 A | 12/1991 | Wustrow et al. | |
| 5,684,018 A | * 11/1997 | Alexander | 514/316 |
| 5,708,177 A | 1/1998 | Straub | |
| 5,756,515 A | 5/1998 | Urbahns et al. | |
| 6,291,454 B1 | 9/2001 | Bullington et al. | |

OTHER PUBLICATIONS

King FD. Medicinal Chemistry: Principles and Practice. The Royal Society of Chemistry. 1994. pp. 206–209.*
Bundgaard H. Design of Prodrugs. Elsevier. 1985. pp. 1–5.*
Biggadike et al.; "Selective Plasma Hydrolysis of Glucocorticoid γ–Lactones and Cyclic Carbonates by the Enzyme Paraoxonase: An Ideal Inactivation Mechanism"; J. Med. Chem. 2000, 43; pp. 19–21.
Lee et al.; "Recent advances in prodrugs and antedrugs"; Current Opinion in Drug Discovery & Development 1998 1(2); pp. 235–244.
Marzabadi et al.; "A Double Protection Strategy for the Synthesis of 3,5–Disubstituted Dihydropyridines"; Tetrahedron Letters 39 (1998); pp. 5293–5296.
Nagarathnam et al.; "Design and Synthesis of Novel $\alpha_{1a}$ Adrenoceptor–Selective Dihydropyridine Antagonists for the Treatment of Benign Prostatic Hyperplasia"; J. Med. Chem. 1998 41:pp. 5320–5333.
Pagani; "Cyclic Sulphones. Part XVIII. Probes for Conjugation of the Sulphonyl Group: Thiopyrano[3,2–b]quinoline 1,1–Dioxides"; J.C.S. Perkin II, 197; pp. 1392–1397.
Dodd, John J., et al.; "Design and Discovery of RWJ 22108—A Novel Bronchoselective Calcium Channel Blocker", Drug Design and Discovery, 1998, vol. 15, pp. 135–148.
Dodd, John H., et al. "Synthesis and Biological Properties of RWJ 22108, A Bronchoselective Calcium Channel Blocker", Drug Design and Discovery, 1993, vol. 10 , pp. 65–75.
International Search Report Application No. PCT/US00/35509 dated May 3, 2001.

* cited by examiner

Primary Examiner—Evelyn Mei Huang

(57) ABSTRACT

This invention provides novel benzoethers of the following formulae:

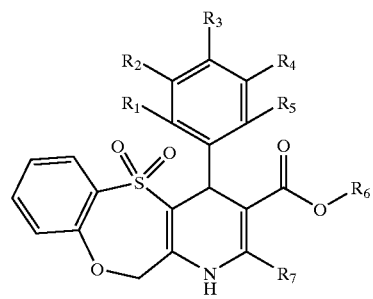

Formula I

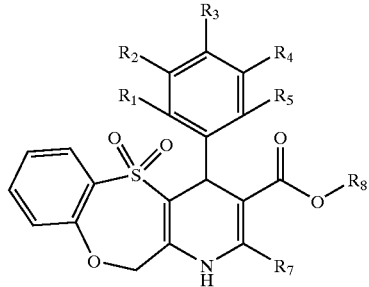

Formula II

These compounds are useful as calcium channel antagonists with cardiovascular, antiasthmatic and antibronchoconstriction activity. Thus, this invention also provides pharmaceutical compositions, as well as methods, for preventing and treating disorders such as hypersensitivity, allergy, asthma, bronchospasm, dysmenorrhea, esophageal spasm, glaucoma, premature labor, urinary tract disorders, gastrointestinal motility disorders and cardiovascular disorders.

24 Claims, No Drawings

BENZOETHER AND RELATED COMPOSITIONS AND METHODS

This application claims the benefit of provisional application No. 60/178,388 filed on Jan. 27, 2000.

FIELD OF THE INVENTION

This invention relates to novel benzoethers useful as calcium channel blockers. These compounds, and related pharmaceutical compositions, are useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

BACKGROUND OF THE INVENTION

Thiacycloalkeno[3,2-b]pyridines are inhibitors of calcium ion uptake into smooth muscle tissue. They act to relax or prevent contraction of the tissue mediated by calcium mechanisms (Dodd et al., Drug Des. Discov. 1997 15:135–48). These compounds are active antihypertensives and bronchodilators.

Thiacycloalkeno[3,2-b]pyridines are also useful for the treatment of cardiovascular disorders, including hypertension, ischemia, angina, congestive heart failure, migraines, myocardial infarction and stroke. Such compounds are also useful for the treatment of other disorders such as hypersensitivity, allergy, asthma, dysmenorrhea, esophageal spasm, gastrointestinal motility disorders, glaucoma, premature labor and urinary tract disorders.

Dodd et al. evaluated a series of thiacycloalkeno[3,2-b] pyridines ranging in sulfone ring size from five to nine members for calcium antagonist activity. It was found that increasing the sulfone ring size from 5 to 8 members results in an in vitro potency increase of two orders of magnitude. Aromatic substitution patterns which favor tracheal effects over aortic effects were found to be 2-$NO_2$ and 2-Cl, 6-F. The ester side chain which was found to maximize in vivo activity was the N-benzyl-N-methyl aminoethyl moiety (Dodd et al., Drug Des. Discov. 1997, 15:135–48, and Drug Des. Discov. 1993, 10:65–75).

Numerous compounds related to thiacycloalkeno[3,2-b] pyridines are known, as exemplified by the following publications. U.S. Pat. No. 5,708,177 to Straub discloses a process for the preparation of optically active ortho-substituted 4-aryl- or heteroaryl-1,4-dihydropyridines by oxidation and subsequent reduction from their opposite enantiomers. U.S. Pat. No. 5,075,440 to Wustrow et al. discloses pyrido[2,3-f][1,4]thiazepines and pyrido[3,2-b][1,5]benzothiazepines which are useful as calcium channel antagonists With cardiovascular, antiasthmatic and antibronchoconstriction activity. U.S. Pat. Nos. 4,879,384 and 4,845,225, both to Schwender and Dodd, disclose substituted thiacycloalkeno [3,2-b] pyridines which are also useful as calcium channel antagonists with cardiovascular, antiasthmatic and antibronchoconstrictor activity. U.S. Pat. Nos. 4,285,955 and 4,483,985 disclose acyclic sulfone substitution simple dihydropyridines which possess calcium channel antagonist activity a. U.S. Pat. No. 4532,248 discloses a broad genus of dihydropyridines, including cyclic sulfones fused to a dihydropyridine nucleus. Cardiotonic activity is disclosed for this entire genus. However, these compounds are not calcium channel blockers. Finally, 10-Phenyl-2H-thiopyranol[3,2-b]quinolines are disclosed in Pagani, G.P.A., J. Chem. Soc. Perkin Trans. 2, 1392 (1974).

"Soft drugs" (also known as "antedrugs") are biologically active drugs which are metabolically inactivated after they achieve their therapeutic role at their designed site of action. The use of soft drugs, instead of their non-inactivatable analogs, avoids unwanted side effects. Soft drugs are known generally (see, for example, Biggadike et al., 2000, J. Med. Chem. 43:19–21; Lee et al., 1998, Curr. Opin. Drug Disc. Dev. 1: 235–44). However, no dihydropyridine soft drugs are known.

SUMMARY OF THE INVENTION

This invention provides novel benzoethers as defined hereinbelow, as well as methods for making same. This invention also provides a pharmaceutical composition comprising the instant compound and a pharmaceutically acceptable carrier.

This invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

Finally, this invention provides an apparatus for administering to a subject the instant pharmaceutical composition, comprising a container and the pharmaceutical composition therein, whereby the container has a means for delivering to the subject a therapeutic and/or prophylactic dose of the pharmaceutical composition.

DETAILED DESCRIPTION OF THE INVENTION

This invention provides a compound of Formula I,

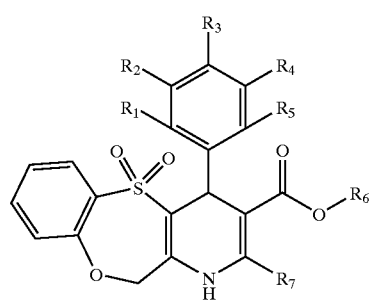

Formula I or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);
(b) $R_6$ is selected from the group consisting of H, $C_{1-5}$ straight or branched alkyl, alkylamine, aryl, 3-piperidyl, N-substituted 3-piperidyl, and N-substituted 2-pyrrolidinyl methylene, wherein said N-substituted 3-piperidyl and said N-substituted 2-pyrrolidinyl methylene may be substituted with C$_{1-8}$ straight or branched chain alkyl or benzyl, and said substituted alkyl may be substituted with C$_{1-8}$ alkoxy, C$_{2-8}$ alkanoyloxy, phenylacetyloxy, benzoyloxy, hydroxy, halogen, p-tosyloxy, mesyloxy, amino, carboalkoxy or NR'R", wherein
(i) R' and R" are independently selected from the group consisting of H, C$_{1-8}$ straight or branched alkyl, C$_{3-7}$ cycloalkyl, phenyl, benzyl, and phenethyl, or (ii) R' and R" together form a heterocyclic ring selected from the group consisting of piperidino, pyrrolidino, morpholino, thiomorpholino, piperazino, 2-thieno, 3-thieno, and an N-substituted derivative of said heterocyclic rings, said N-substituted derivative being substituted with H, C$_{1-8}$ straight or branched alkyl, benzyl, benzhydryl, phenyl and/or substituted phenyl (substituted with NO$_2$, halogen, C$_{1-8}$ straight or branched chain alkyl, C$_{1-8}$ alkoxy and/or trifluoromethyl); and
(c) R$_7$ is selected from the group consisting of H, amino, alkyl, aryl, thifloromethyl, alkoxymethyl, 2-thieno and 3-thieno.

The following compounds are embodiments of the present invention:

1H-[1,5]Benzoxathiepino[3,4-b]pyridine-3-carboxylic acid, 4-(2-chlorophenyl)-4,11-dihydro-2-methyl-, methyl ester, 5,5-dioxide;

1H-[1,5]Benzoxathiepino[3,4-b]pyridine-3-carboxylic acid, 4-(2-chlorophenyl)-4,11-dihydro-2-methyl-, 2-[methyl(phenylmethyl)amino]ethyl ester, 5,5-dioxide;

1H-[1,5]Benzoxathiepino[3,4-b]pyridine-3-carboxylic acid, 4-(3-chlorophenyl)-4,11-dihydro-2-methyl-, 2-[methyl(phenylmethyl)amino]ethyl ester, 5,5-dioxide;

1H-[1,5]Benzoxathiepino[3,4-b]pyridine-3-carboxylic acid, 4-(2,3-dichlorophenyl)4,11-dihydro-2-methyl-, 2-[methyl(phenylmethyl)amino]ethyl ester, 5,5-dioxide;

1H-[1,5]Benzoxathiepino[3,4-b]pyridine-3-carboxylic acid, 4,11-dihydro-2-methyl-4-(3-nitrophenyl)-, methyl ester, 5,5-dioxide;

1H-[1,5]Benzoxathiepino[3,4-b]pyridine-3-carboxylic acid, 4-(2-chloro-6-fluorophenyl)4,11-dihydro-2-methyl-, 2-[methyl(phenylmethyl)amino]ethyl ester, 5,5-dioxide; and 1H-[1,5]Benzoxathiepino[3,4-b]pyridine-3-carboxylic acid, 4,11-dihydro-2-methyl-4-(3-nitrophenyl)-, 2-[methyl(phenylmethyl)amino]ethyl ester, 5,5-dioxide.

This invention also provides soft drug analogs of the compounds of Formula I. These soft drugs are characterized by a chemically labile moiety bound to the ester group in turn bound to the dihydropyridine ring structure. The soft drugs permit the instant drugs to exert their effect locally, and to subsequently be metabolized in the blood stream, thereby reducing unwanted systemic effects (e.g. low blood pressure). Use of such soft drug analogs permits the administration of greater doses of the claimed dihydropyridine compounds without subjecting the subject to intolerable levels of unwanted systemic effects.

Specifically, this invention provides a compound of Formula II,

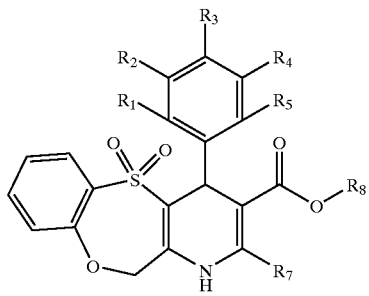

Formula II or a pharmaceutically acceptable salt thereof, wherein
(a) R$_1$, R$_2$, R$_3$, R$_4$ and R$_5$ are independently selected from the group consisting of H, OH, halogen, cyano, NO$_2$, alkyl, C$_{1-8}$ alkoxy, C$_{1-8}$ alkylsulfonyl, C$_{1-4}$ carboalkoxy, C$_{1-8}$ alkylthio, difluoromethoxy, difluoromethylthio, trifluoromethyl, and oxadiazole (formed by R$_1$ and R$_2$);
(b) R$_7$ is selected from the group consisting of H, amino, alkyl, aryl, trifluoromethyl, alkoxymethyl, 2-thieno and 3-thieno; and
(c) R$_8$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-OC(O)R''', -alkyl-C(O)R''', -alkyl-C(O)OR''', -alkyl-N(R")C(O)R''', and -alkyl-N(R"")C(O)OR''', wherein
R''' and R"" are independently selected from the group consisting of hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, NO$_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, NO$_2$, alkyl, amino, dimethylamino, alkoxy, alkylsulfonyl, C$_{1-4}$ carboalkoxy, alkylthio and/or trifluoromethyl).

Each of the embodiments of the compound of Formula I set forth above is also contemplated as an embodiment of the compound of Formula II. In addition, in one embodiment of Formula II, R$_7$ is methyl and R$_1$, R$_2$, R$_3$, R$_4$, and R$_5$ are independently selected from hydrogen, halogen, trifluoromethyl and NO$_2$. In another embodiment of Formula II, R$_8$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-C(O)R''', -alkyl-N(R")C(O)R''', and -alkyl-N(R"")C(O)OR'''. More particularly, R$_8$ is selected from the group consisting of —(CH$_2$)$_2$OC(O)CH(CH$_2$CH$_3$)$_2$, —(CH$_2$)$_2$OC(O)CH(CH$_3$)$_2$, —(CH$_2$)$_2$OC(O)PH—OCH(CH$_3$)$_2$, —CH$_2$OC(O)CH$_2$N(CH$_3$)CH$_2$PH, —CH$_2$OC(O)CH$_2$—PH—N(CH$_3$)$_2$, and —CH$_2$OC(O)CH(CH$_2$)$_6$.

Unless specified otherwise, the term "alkyl" refers to a straight, branched or cyclic substituent consisting solely of carbon and H with no unsaturation. Alkyl may be substituted by, for example, OH, halogen, cyano, NO$_2$, alkyl, C$_{1-8}$ alkoxy, C$_{1-8}$ alkylsulfonyl, C$_{1-4}$ carboalkoxy, and C$_{1-8}$ alkylthio. The term "alkoxy" refers to O-alkyl where alkyl is as defined. Aryl substituents include, for example, phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ar" may be aryl or heteroaryl. The term "heterocyclyi", "heterocycle" or "heterocyclic residue" represents a single or fused ring or rings having at least one atom other than carbon as ring member, e.g. pyridine, pyrimidine, oxazoline, pyrrole, imidazole, morpholine, furan, indole, benzofuran, pyrazole, pyrrolidine, piperidine, thiophene, and benzimidazole. Illustrative alkylamines include —(CH$_2$)$_2$N(Me)CH$_2$(Ar) such as —(CH$_2$)$_2$N(Me)CH$_2$ (PH) and —CH$_2$CH$_2$—N(Me)—CH$_2$(heteroaryl). The symbol "Ph" or "PH" refers to phenyl. The term "halo" means fluoro, chloro, bromo or iodo. A "dehydrating agent," which is used in a solvent such as CH$_2$Cl$_2$ or toluene, includes but is not limited to sulfuric acid and acetic anhydride. "Independently" means that when there are more than one substituent, the substitutents may be different.

The compounds of the instant invention are asymmetric in the dihydropyridine ring at the 4-position and thus exist as optical antipodes. As such, all possible optical isomers, antipodes, enantiomers, and diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle-type column.

As used herein, the phrase "pharmaceutically acceptable salt" means a salt of the free base which possesses the desired pharmacological activity of the free base and which is neither biologically nor otherwise undesirable. These salts may be derived from inorganic or organic acids. Examples of inorganic acids are hydrochloric acid, nitric acid, hydrobromic acid, sulfuric acid, and phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like.

The instant compounds can be prepared using readily available starting materials and reaction steps well known in the art (Edema et al. J. Org. Chem. 58: 5624–7, 1993; Howard et al., J. Amer. Chem. Soc. 82:158–64, 1960).

This invention also provides a pharmaceutical composition comprising the instant compound and a pharmaceutically acceptable carrier.

Pharmaceutical compositions containing a compound of the present invention as the active ingredient in intimate admixture with a pharmaceutical carrier can be prepared according to conventional pharmaceutical techniques. The carrier may take a wide variety of forms depending on the form of preparation desired for administration, such as systemic administration including but not limited to intravenous, oral, nasal or parenteral. In preparing the compositions in oral dosage form, any of the usual pharmaceutical carriers may be employed, such as water, glycols, oils, alcohols, flavoring agents, preservatives, coloring agents, syrup and the like in the case of oral liquid preparations (for example, suspensions, elixirs and solutions), and carriers such as starches, sugars, diluents, granulating agents, lubricants, binders, disintegrating agents and the like in the case of oral solid preparations (for example, powders, capsules and tablets).

In one embodiment, the compounds of the instant invention are administered by inhalation. For inhalation administration, the compounds can be in a solution intended for administration by metered dose inhalers, or in a form intended for a dry powder inhaler or insufflator. More particularly, the instant compounds can be conveniently delivered in the form of an aerosol spray from a pressurized container, a pack or a nebuliser with the use of a suitable propellant, e.g., dichlorodifluoromethane, trichlorofluoromethane, dichlorotetrafluoroethane, carbon dioxide or other suitable gas. The dosage unit may be determined by providing a valve to deliver a metered amount. Capsules and cartridges made of a pharmaceutically acceptable material such as gelatin for use in an inhaler or insufflator can be formulated to contain a powder mix of the compound and a suitable powder base such as lactose or starch.

Because of their ease of administration, tablets and capsules represent an advantageous oral dosage unit form wherein solid pharmaceutical carriers are employed. If desired, tablets can be sugar-coated or enteric-coated by standard techniques. For parenterals, the carrier will usually comprise sterile water, though other ingredients to aid solubility or to act as preservatives can be included. Injectable suspensions can also be prepared, wherein appropriate liquid carriers, suspending agents and the like are employed. The instant compounds can also be administered in the form of an aerosol, as discussed above.

The instant pharmaceutical composition can contain per dosage unit (e.g., tablet, capsule, powder, injection, teaspoonful and the like) from about 0.001 to about 100 mg/kg, and preferably from about 0.01 to about 20 mg/kg of the instant compound.

The compounds of the present invention inhibit the uptake of calcium ions into smooth muscle cells, and therefore act to relax or prevent calcium ion-mediated contraction of smooth muscle tissue.

Thus, this invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition. By way of example, in a subject suffering from asthma, the subject's airways are constricted due to inflammation of airway smooth muscle cells ("SMC's"). Reducing the calcium influx into the SMC's, whose action (i.e., inflammation) contributes to the disorder, would be expected to alleviate the disorder.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

In one embodiment, the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder. In the preferred embodiment, the disorder is asthma. The cardiovascular disorder can be, for example, hypertension, ischemia, angina, congestive heart failure, myocardial infarction or stroke.

As used herein, "treating" a disorder means eliminating or otherwise ameliorating the cause and/or effects thereof. "Inhibiting" the onset of a disorder means preventing, delaying or reducing the likelihood of such onset.

The term "subject" includes, without limitation, any animal or artificially modified animal. In the preferred embodiment, the subject is a human.

Methods are known in the art for determining therapeutically and prophylactically effective doses for the instant pharmaceutical composition. The effective dose for administering the pharmaceutical composition to a human, for example, can be determined mathematically from the results of animal studies.

This invention further provides an apparatus for administering to a subject the instant pharmaceutical composition, comprising a container and the pharmaceutical composition therein, whereby the container has a means for delivering to the subject a therapeutic and/or prophylactic dose of the pharmaceutical composition. In the preferred embodiment, the apparatus is an aerosol spray device for treating and/or preventing asthma via topical respiratory administration.

Finally, this invention provides a process for preparing the compound of Formula I.

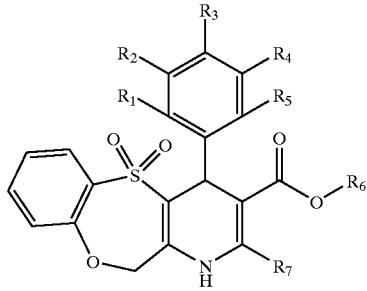

Formula I which process comprises:
(a) reacting Compound 1a with Compound 1b to form Compound 1c;

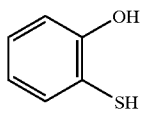

1a

1b

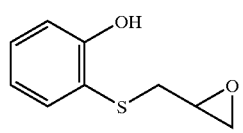

1c

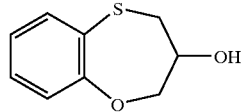

1d (b) converting Compound 1c to Compound 1d in presence of $H_2O$ and NaOH;
(c) converting Compound 1d to Compound 1e in presence of MTO, AcOH, and $H_2O_2$;

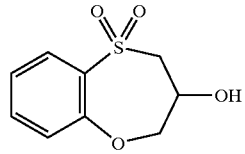

1e

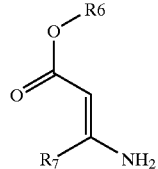

1h

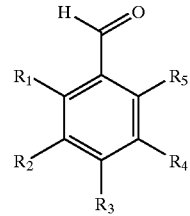

1g

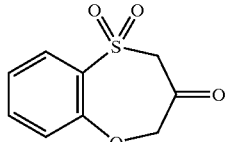

1f (d) converting Compound 1e to Compound 1f in presence of Jones Reagent and acetone; and
(e) reacting Compound 1f with Compounds 1h and 1g to form the compound of Formula I.

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

A. Schemes and Syntheses

The compounds of Formula I can be made in accordance with the following general procedures outlined in Scheme I:

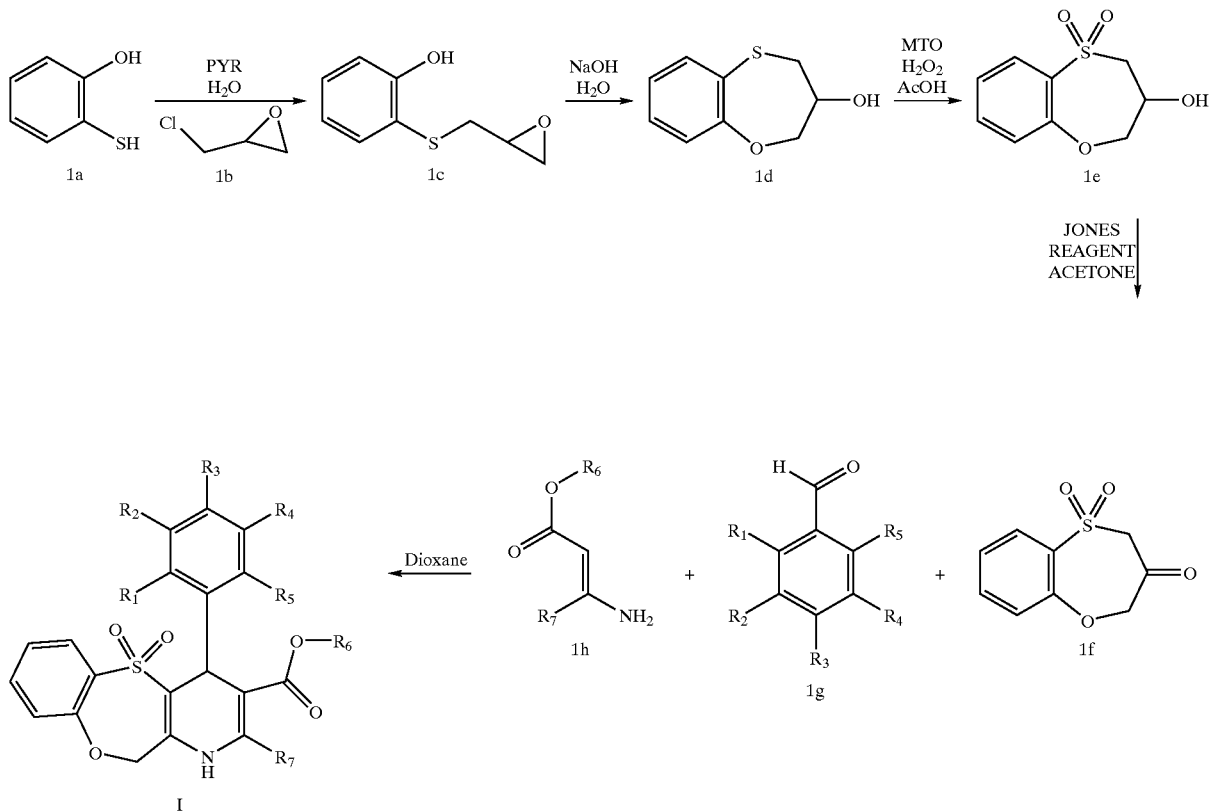

Procedures for making dihydropyrides are well documented in the art as shown in Eistert et al. (Chem. Ber. 110, 1069–1085, 1977), G. A. Pagani (J. Chem. Soc., Perkin Trans. 2, 1392–7, 1974), Mason et al. (J. Chem. Soc. (C) 2171–76, 1967), E. A. Fehnel (J. Amer. Chem. Soc. 74, 1569–74, 1952), and M. Seiyaku (Japan Patent Application No. 58201764, 1984).

The compounds of Formula II can be made in accordance with Scheme II, wherein $R_{1-8}$ are as described above, preferably in the presence of $K_2CO_3$ or $CsCO_3$ in an organic solvent such as dimethylformamide (DMF).

Scheme II

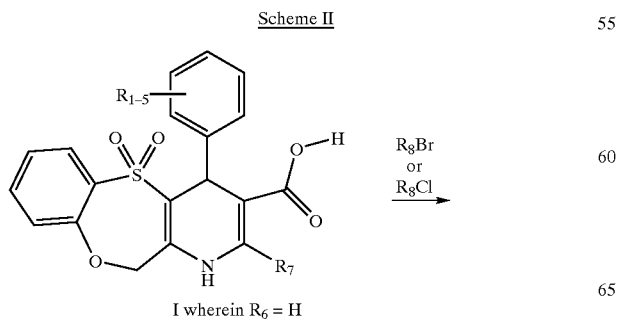

-continued

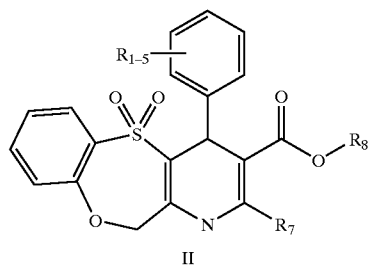

The compounds of Formula II may also be made in accordance with Scheme III, wherein $R_{1-8}$ are as described above, preferably in the presence of formic acid or NaOH (aq), respectively.

Scheme III

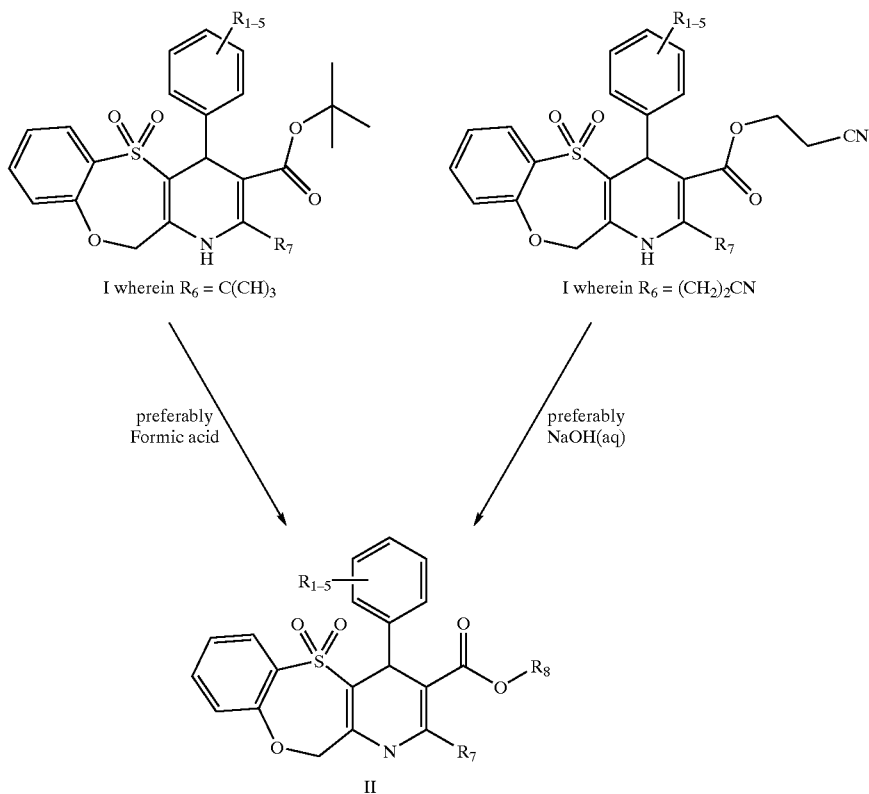

The Examples below describe in greater detail the chemical syntheses of representative compounds of the present invention. The remaining compounds disclosed herein can be prepared similarly in accordance with one or more of these methods. No attempt has been made to optimize the yields obtained in these syntheses, and it would be clear to one skilled in the art that variations in reaction times, temperatures, solvents, and/or reagents could be used to increase such yields.

Table 1 below sets forth the mass spectra data, the inhibition of nitrendipine binding and inhibition of calcium-dependent smooth muscle contraction for the instant compounds tested.

TABLE 1

Molecular Weight, Mass Spectra Data and
Calcium Channel Antagonist Activity for Compounds 1–7

Formula Ia

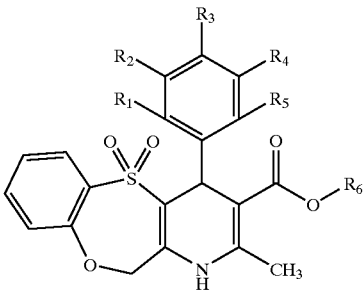

| Compound No. | $R_1$ | $R_2$ | $R_3$ | $R_4$ | $R_5$ | $R_6$ | Mol. Wt. | Mass Spectroscopy | Nitrendipine Binding Assay $IC_{50}nM$ |
|---|---|---|---|---|---|---|---|---|---|
| 1 | H | H | H | H | Cl | Me | 431.8964 | — | 61 |
| 2 | H | H | H | H | Cl | $(CH_2)_2N(CH_3)CH_2Ph$ | 601.55 | M + H = 565 | 59 |

TABLE 1-continued

Molecular Weight, Mass Spectra Data and
Calcium Channel Antagonist Activity for Compounds 1–7

Formula Ia

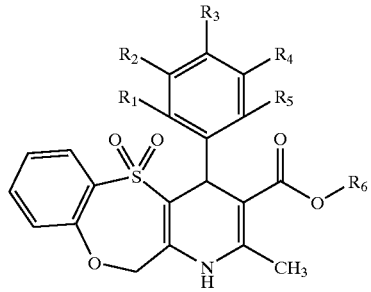

| Compound No. | $R_1$ | $R_2$ | $R_3$ | $R_4$ | $R_5$ | $R_6$ | Mol. Wt. | Mass Spectroscopy | Nitrendipine Binding Assay $IC_{50}$ nM |
|---|---|---|---|---|---|---|---|---|---|
| 3 | H | H | H | $NO_2$ | H | Me | 442.4492 | M + Na = 465 | 33 |
| 4 | H | H | H | $NO_2$ | H | $(CH_2)_2N(CH_3)CH_2Ph$ | 612.1029 | M + H = 576 | 45 |
| 5 | H | H | H | Cl | H | $(CH_2)_2N(CH_3)CH_2Ph$ | 601.55 | M + H = 565 | 109 |
| 6 | H | H | H | Cl | Cl | $(CH_2)_2N(CH_3)CH_2Ph$ | 635.9948 | M + H = 599 | 21 |
| 7 | F | H | H | H | Cl | $(CH_2)_2N(CH_3)CH_2Ph$ | 681.0748 | M + H = 583 | 47 |

EXAMPLE 1

1H-[1,5]Benzoxathiepino[3,4-b]pyridine-3-carboxylic acid, 4-(2-chloro-6-fluorophenyl)-4,11-dihydro-2-methyl-, 2-[methyl(phenylmethyl)amino]ethyl ester, 5,5-dioxide (Compound 7)

Scheme II

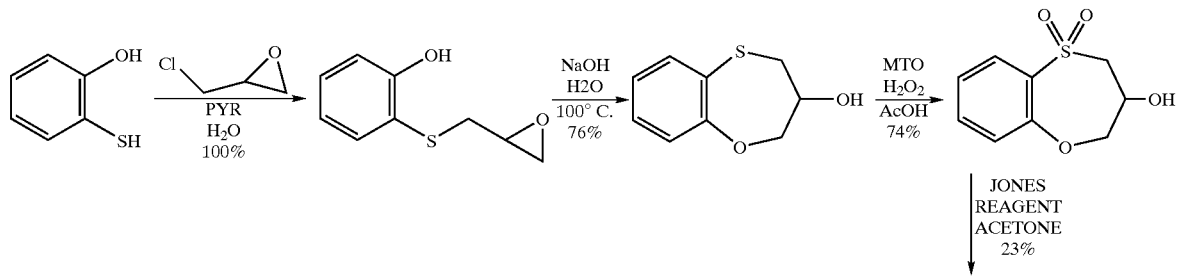

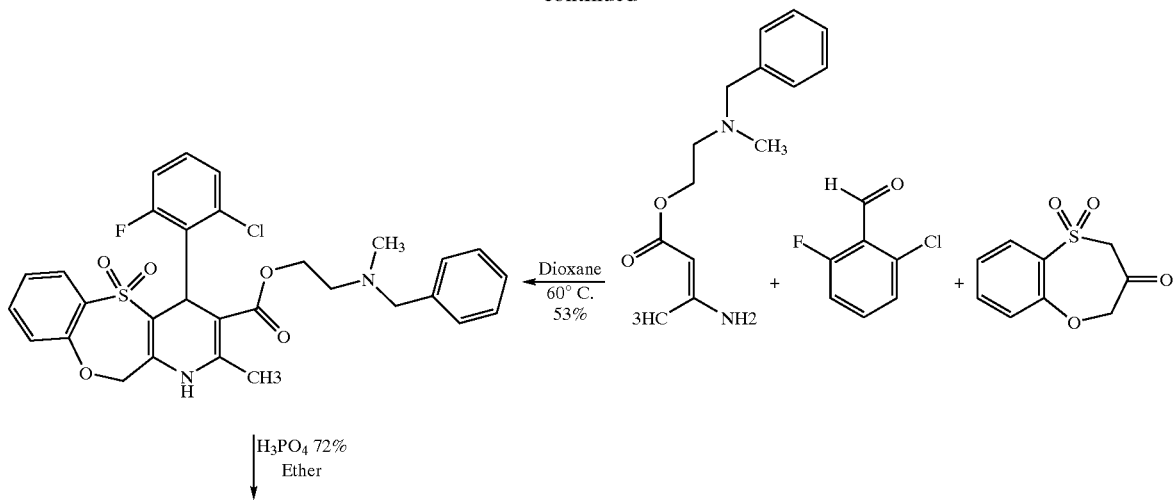

Compound 7 was prepared following Scheme II above. The details of the preparation are as follows:

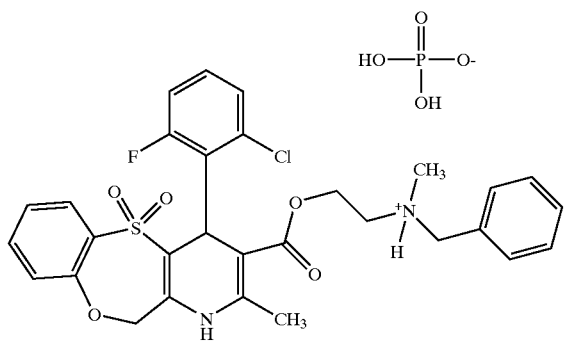

19.61 g (211.92 mmoles) of epichlorohydrin was added dropwise by syringe to a solution of 26.74 g (211.92 mmoles) of 2-Hydroxythiophenol in 75 ml water containing 16.76 g (211.92 mmoles) pyridine. The resultant solution was stirred at room temperature for 18 hours. The reaction was then made acidic with 1N HCl solution and extracted 1×250 ml CHCl$_3$. The organic layer was separated, dried over MgSO$_4$, filtered and concentrated in vacuo to give 40.3 g of an orange oil (>100% yield). This procedure is described in Cabiddu et al., Heterocyclic compounds studies; synthesis of 1,5-benzoxathiepines, Phosphorus Sulfur (1983), 14(2), pp.151–6. CODEN: PREEDF ISSN:0308-664X. CAN 98:215576; AN 1983:215576 CAPLUS.

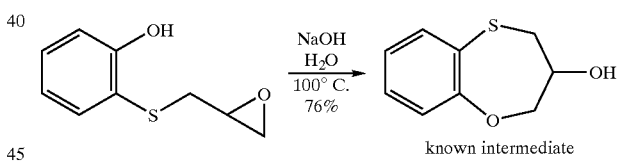

A mixture of 40.3 g (221.14 mmoles) of the epoxide was refluxed in 88 ml of water containing 8.85 g (221.14 mmoles) sodium hydroxide for five hours. The reaction was cooled to room temperature and made acidic with 1N HCl, the extracted 2×200 ml EtOAc. The organic layers were separated, combined, washed 2×100 ml water, dried over MgSO$_4$, filtered, and concentrated in vacuo to give 30.77 g of a brown semi-solid. This procedure is described in Sugihara et al., 1,5-Benzoxathiepin derivatives. I. Synthesis and reaction of 1,5-benzoxathiepin derivatives., Chem. Pharm. Bull. (1987), 35(5), pp.1919–29. CODEN: CPBTAL ISSN:0009-2363. CAN 108:75371; AN 1988:75371 CAPLUS.

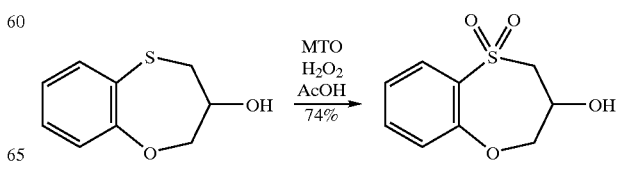

A solution of 30.77 g (168.84 mmoles) of the sulfide in 100 ml acetic acid containing 0.50 g (2.00 mmoles) Methyl (trioxorheniumVII) was cooled to 0° C. 100 ml of 30% hydrogen peroxide in water solution were added dropwise by addition funnel. The reaction was stirred at room temperature for seven hours, then diluted with 300 ml water and extracted 2×500 ml EtOAc. The organic layers were separated, combined, washed 4×500 ml water, 1×100 ml brine, dried over MgSO$_4$, filtered, and concentrated in vacuo to give 22.61 g (124.21 mmoles) of the sulfone as a light brown oil.

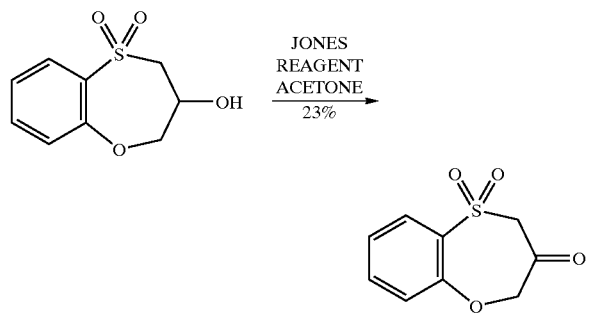

To 26.61 g (124.21 mmoles) of the alcohol in 250 ml acetone at 0° C. was added 51 ml (136.63 mmoles) of freshly prepared 2.7M Jones Reagent dropwise by addition funnel. The Jones Reagent was prepared by carefully dissolving 13.4 g of chromium trioxide in 12 ml of concentrated sulfuric acid then carefully diluting to 51 ml total volume with water. The cooling bath was removed and the resultant slurry was stirred at room temperature 18 hours. The reaction was then diluted with 200 ml water and extracted 3×400 ml EtOAc. The organic layers were separated, combined, and washed 2×200 ml water, 1×200 ml brine, dried over MgSO$_4$, filtered, and concentrated in vacuo to 34 g of a thick brown oil. Column chromatography using 2:1 Hexane/EtOAc as eluent afforded a colorless oil the solidified upon treatment with ether to give 6.19 g of white solid.

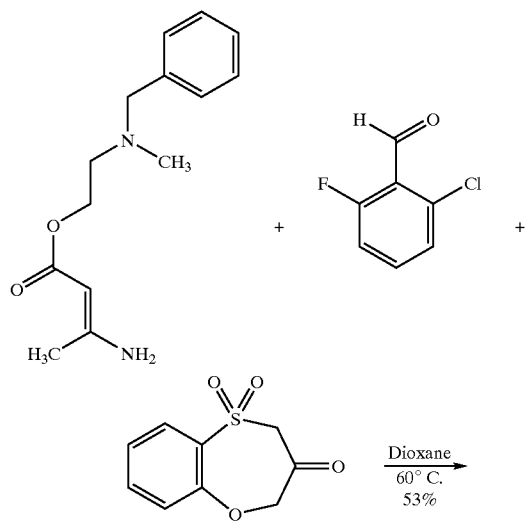

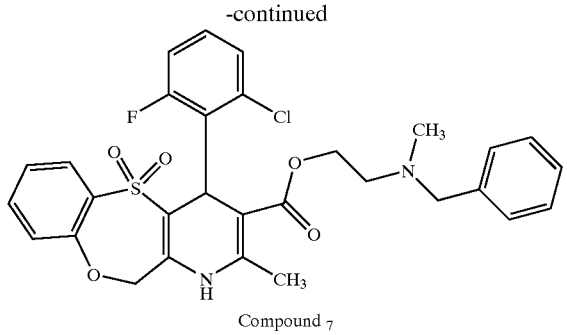

Compound 7

A solution of 1.58 g (7.44 mmoles) of the benzosulfone ether, 1.18 g (7.44 mmoles) of 2-Chloro-6-fluorobenzaldehyde and 1.85 g (7.44 mmoles) of 2-(N-benzyl-N-methylamino)ethyl-3-aminocrotonate in 30 ml Dioxane was heated to 60° C. for 18 hours. The reaction was cooled and the dioxane removed in vacuo. The residue as dissolved in 5 ml of EtOAc and subjected to column chromatography using 2:1 Hexane/Ethyl acetate as eluent, affording 2.30 g (3.94 mmoles) of a light yellow foam.

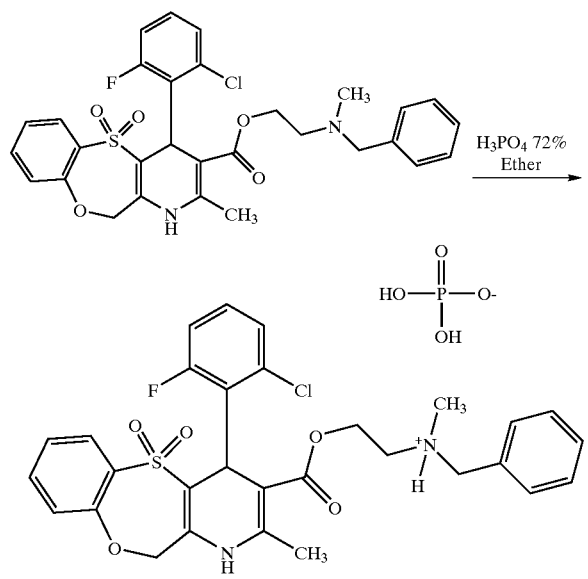

Compound 7

2.30 g (3.94 mmoles) of the dihydropyridine was dissolved in 150 ml diethyl ether. A solution of 0.46 g (3.94 mmoles) 85% o-phosphoric acid in 100 ml of diethyl ether was added dropwise by addition funnel. The resultant slurry was stirred for one hour, filtered and the precipitate was washed with diethyl ether to give (1.95 g (2.86 mmoles) of the phosphate salt.

B. Assays

EXAMPLE 2

Assay for Inhibition of Nitrendipine Binding

Female, New Zealand white rabbits (1–2 kg) are sacrificed by cervical dislocation, and the heart is immediately removed, cleaned and chopped into small pieces. The tissue is homogenized in 5×times volume of 0.05M Hepes buffer, pH 7.4. The homogenate is centrifuged at 4000 g for 10 minutes, and the supernatant is re-centrifuged at 42,000×g for 90 minutes. The resulting membrane pellet is resuspended (0.7 ml/g weight) in 0.05M Hepes, pH 7.4 and stored at 70° C. until used. Each tube of the binding assay contains $^3$H-nitrendipine (0.05–0.50 nM), buffer, membranes (0.10 ml), and test compound in a total volume of 1.0 ml. After 90 minutes at 4° C., the bound nitrendipine is separated from the unbound by filtration on Whatman GF/C filters. After rinsing, the filters are dried and counted in a liquid scintillation counter.

Non-specific binding of $^3$H-nitrendipine (that amount bound in the presence of excess unlabelled nitrendipine) is subtracted from the total bound to obtain specifically bound radiolabeled nitrendipine. The amount of specifically bound nitrendipine in the presence of a test compound is compared to that amount bound in the absence of a compound. A percent displacement (or inhibition) can then be calculated.

EXAMPLE 3

Test for Inhibition of Calcium-Dependent Smooth Muscle Contraction

The trachea and the aorta from dogs sacrificed by excess KCl injection are stored overnight at 4° C. in oxygenated Krebs-Henseleit buffer. Tracheal rings, one cartilage segment wide (5–10 mm), are cut starting from the bronchial end. Rings of aorta tissue of the same width are also prepared. After cutting the cartilage, the trachealis muscle tissue and the aorta tissue are suspended in oxygenated Krebs-Henseleit buffer at 37° C. in a 25 ml tissue bath. After a 60-minute equilibration period, the tissues are challenged with 10 μM carbachol. After 5 minutes, the tissues are rinsed and allowed to rest 50 minutes. The tissues are then challenged with 50 mM KCl and, after 30 minutes, the contractions are quantitated. The tissues are then rinsed and re-equilibrated for 50 minutes. Test compounds are then added for 10 minutes, and the tissue is rechallenged with 50 mM KCl. After 30 minutes, the contraction is recorded. A percent inhibition of smooth muscle contraction can then be calculated.

What is claimed is:

1. A compound of Formula I,

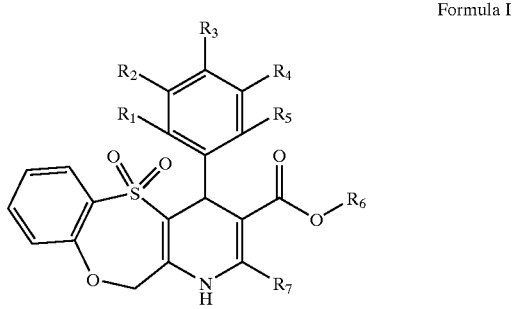

Formula I or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, and trifluoromethyl; or $R_1$ and $R_2$ together form an oxadiazole;
(b) $R_6$ is selected from the group consisting of H, $C_{1-5}$ straight or branched alkyl, alkylamine, aryl, 3-piperidyl, N-substituted 3-piperidyl, and N-substituted 2-pyrrolidinyl methylene, wherein said N-substituted 3-piperidyl and said N-substituted 2-pyrrolidinyl methylene may be substituted with $C_{1-8}$ straight or branched chain alkyl or benzyl, and said straight or branched alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein
(i) R' and R" are independently selected from the group consisting of H, $C_{1-8}$ straight or branched alkyl, $C_{3-7}$ cycloalkyl, phenyl, benzyl, and phenethyl, or
(ii) R' and R" together form a heterocyclic ring selected from the group consisting of piperidino, pyrrolidino, morpholino, thiomorpholino, piperazino, and an N-substituted piperazino ring, said N-substituted piperazino ring being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trifluoromethyl); and (c) $R_7$ is selected from the group consisting of H, amino, alkyl, aryl, trifluoromethyl, alkoxymethyl, 2-thieno and 3-thieno.

2. The compound of claim 1, wherein $R_6$ is methyl.

3. The compound of claim 2, wherein $R_4$ is $NO_2$ and $R_7$ is methyl.

4. The compound of claim 1, wherein $R_6$ is —$(CH_2)_2$N$(CH_3)CH_2$Ph.

5. The compound of claim 4, wherein $R_4$ and $R_5$ are Cl, and $R_7$ is methyl.

6. The compound of claim 1 which is 1H-[1,5] Benzoxathiepino[3,4-b]pyridine-3-carboxylic acid, 4-(2-chlorophenyl)-4,11-dihydro-2-methyl-, methyl ester, 5,5-dioxide.

7. The compound of claim 1 which is 1H-[1,5] Benzoxathiepino[3,4-b]pyridine-3-carboxylic acid, 4-(2-chlorophenyl)-4,11-dihydro-2-methyl-, 2-[methyl (phenylmethyl)amino]ethyl ester, 5,5-dioxide.

8. The compound of claim 1 which is 1H-[1,5] Benzoxathiepino[3,4-b]pyridine-3-carboxylic acid, 4-(3-chlorophenyl)-4,11-dihydro-2-methyl-, 2-[methyl (phenylmethyl)amino]ethyl ester, 5,5-dioxide.

9. The compound of claim 1 which is 1H-[1,5] Benzoxathiepino[3,4-b]pyridine-3-carboxylic acid, 4-(2,3-dichlorophenyl)-4,11-dihydro-2-methyl-, 2-[methyl (phenylmethyl)amino]ethyl ester, 5,5-dioxide.

10. The compound of claim 1 which is 1H-[1,5] Benzoxathiepino[3,4-b]pyridine-3-carboxylic acid, 4,11-dihydro-2-methyl-4-(3-nitrophenyl)-, methyl ester, 5,5-dioxide.

11. The compound of claim 1 which is 1H-[1,5] Benzoxathiepino[3,4-b]pyridine-3-carboxylic acid, 4-(2-chloro-6-fluorophenyl)-4,11-dihydro-2-methyl-, 2-[methyl (phenylmethyl)amino]ethyl ester, 5,5-dioxide.

12. The compound of claim 1 which is 1H-[1,5] Benzoxathiepino[3,4-b]pyridine-3-carboxylic acid, 4,11-dihydro-2-methyl-4-(3-nitrophenyl)-, 2-[methyl (phenylmethyl)amino]ethyl ester, 5,5-dioxide.

13. A compound of Formula II,

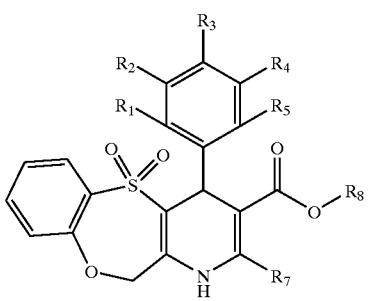

Formula II or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, and trifluoromethyl; or $R_1$ and $R_2$ together form an oxadiazole;
(b) $R_7$ is selected from the group consisting of H, amino, alkyl, aryl, trifluoromethyl, alkoxymethyl, 2-thieno and 3-thieno; and
(c) $R_8$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-OC(O)R''', -alkyl-C(O)R''', alkyl-C(O)OR''', -alkyl-N(R'')C(O)R''', and -alkyl-N(R'')C(O)R''', wherein N(R''')C(O)OR''', wherein
R''' and R'''' are independently selected from the group consisting of hydrogen, amino, alkyl, aryl, aryl-fused cycloalkyl and heterocyclyl, the amino, alkyl, aryl, aryl-fused cycloalkyl and heterocyclyl being optionally substituted with at least one substituent selected from the group consisting of halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and aryl (the aryl being optionally substituted with at least one substituent selected from the group consisting of OH, halogen, cyano, $NO_2$, alkyl, amino, dimethylamino, alkoxy, alkylsulfonyl, $C_{1-4}$ carboalkoxy, alkylthio and trifluoromethyl).

14. The compound of claim 13 wherein $R_7$ is methyl and $R_1$, $R_2$, $R_3$, $R_4$, and $R_5$ are independently selected from hydrogen, halogen, trifluoromethyl and $NO_2$.

15. The compound of claim 13 wherein $R_8$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-C(O)R''', -alkyl-N(R'')C(O)R''', and -alkyl-N(R''')C(O)OR'''.

16. The compound of claim 13 wherein $R_8$ is selected from the group consisting of —$(CH_2)_2OC(O)CH(CH_2CH_3)_2$, —$(CH_2)_2OC(O)CH(CH_3)_2$, —$(CH_2)_2OC(O)Ph$—$OCH(CH_3)_2$, —$CH_2OC(O)CH_2N(CH_3)CH_2Ph$, —$CH_2OC(O)CH_2$—$Ph$—$N(CH_3)_2$, and —$CH_2OC(O)CH(CH_2)_6$.

17. A pharmaceutical composition comprising the compound of claim 1 or 13 and a pharmaceutically acceptable carrier.

18. A method of treating a subject suffering from a disorder whose alleviation is mediated by the reduction of calcium ion influx into cells whose actions contribute to the disorder, which method comprises administering to the subject a therapeutically effective dose of the pharmaceutical composition of claim 17.

19. The method of claim 18, wherein the subject has normal or low blood pressure.

20. The method of claim 18, wherein the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder.

21. The method of claim 20, wherein the disorder is asthma.

22. The method of claim 20, wherein the cardiovascular disorder is selected from the group consisting of hypertension, ischemia, angina, congestive heart failure, myocardial infarction and stroke.

23. An apparatus for administering to a subject the pharmaceutical composition of claim 17, comprising a container and the pharmaceutical composition therein, whereby the container has a means for delivering to the subject a therapeutic and/or prophylactic dose of the pharmaceutical composition.

24. A process for preparing the compound of Formula I of claim 1

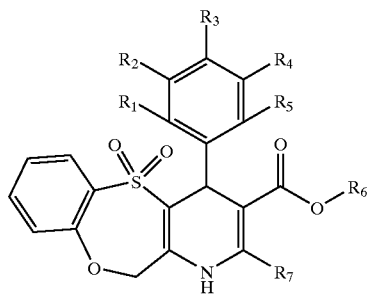

Formula I which process comprises:
(a) reacting Compound 1a with Compound 1b to form Compound 1c;

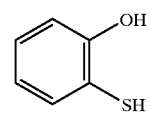

1a

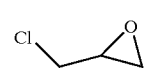

1b

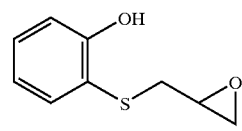

1c

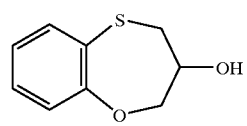

1d